(12) United States Patent
Meyer et al.

(10) Patent No.: US 8,821,405 B2
(45) Date of Patent: Sep. 2, 2014

(54) CABLE MONITORING APPARATUS

(75) Inventors: Peter F Meyer, Shrewsbury, MA (US); Eliot Zaiken, Sparta, NJ (US)

(73) Assignee: Covidien LP, Mansfield, MA (US)

( * ) Notice: Subject to any disclaimer, the term of this patent is extended or adjusted under 35 U.S.C. 154(b) by 12 days.

(21) Appl. No.: 13/344,018

(22) Filed: Jan. 5, 2012

(65) Prior Publication Data

US 2012/0130239 A1    May 24, 2012

Related U.S. Application Data

(62) Division of application No. 11/528,914, filed on Sep. 28, 2006, now Pat. No. 8,109,883.

(51) Int. Cl.
*A61B 5/03* (2006.01)
*A61B 5/00* (2006.01)
*A61B 5/103* (2006.01)
*A61B 5/117* (2006.01)

(52) U.S. Cl.
USPC ............ 600/528; 600/300; 600/587; 600/588

(58) Field of Classification Search
USPC .................................. 600/528, 300, 587, 588
See application file for complete search history.

(56) References Cited

U.S. PATENT DOCUMENTS

| | | | |
|---|---|---|---|
| 3,606,881 A | 9/1971 | Woodson | |
| 3,752,151 A | 8/1973 | Robichaud | |
| 3,805,769 A | 4/1974 | Sessions | |
| 3,828,766 A | 8/1974 | Krasnow | |
| 3,868,946 A | 3/1975 | Hurley | |
| 3,888,240 A | 6/1975 | Reinhold, Jr. et al. | |
| 3,895,635 A | 7/1975 | Justus et al. | |
| 3,901,218 A | 8/1975 | Buchalter | |
| 3,997,225 A | 12/1976 | Horwinski | |
| 3,998,213 A | 12/1976 | Price | |
| 4,027,664 A | 6/1977 | Heavner, Jr. et al. | |
| 4,034,854 A | 7/1977 | Bevilacqua | |
| 4,077,397 A | 3/1978 | Ellis et al. | |
| 4,112,941 A | 9/1978 | Larimore | |
| 4,166,465 A | 9/1979 | Esty et al. | |
| 4,256,118 A | 3/1981 | Nagel | |

(Continued)

FOREIGN PATENT DOCUMENTS

| | | |
|---|---|---|
| DE | 9002539 U1 | 5/1990 |
| DE | 10225621 | 1/2004 |

(Continued)

OTHER PUBLICATIONS

A&D Company, Limited, "Vital Sensor Graphic Model", No. TM-2560G/TM2564G-TM-2564GP/TM2564GP, Jan. 1, 2004; pp. 1-62.

(Continued)

*Primary Examiner* — Sean Dougherty
(74) *Attorney, Agent, or Firm* — Lisa E. Winsor, Esq.

(57) ABSTRACT

A cable monitoring apparatus includes a housing having an input interface adapted to electrically connect to one end of a medical cable and an output interface adapted to electrically connect to an electrical system. Signal processing circuitry is incorporated within the housing for receiving a medical signal from the medical cable via the input interface and for selectively passing the medical signal to the electrical system via the output interface when in a first mode of operation, and has application software for selectively testing functionality of the medical cable when in a second mode of operation. The medical signal may include at least one monitoring signal selected from a group consisting of fetal and maternal medical signals.

10 Claims, 4 Drawing Sheets

(56) References Cited

U.S. PATENT DOCUMENTS

| | | | |
|---|---|---|---|
| 4,353,372 | A | 10/1982 | Ayer |
| 4,365,634 | A | 12/1982 | Bare et al. |
| 4,378,021 | A | 3/1983 | Strand |
| 4,385,272 | A | 5/1983 | Whitehead |
| 4,477,801 | A | 10/1984 | Robinson et al. |
| 4,498,480 | A | 2/1985 | Mortensen |
| 4,729,377 | A | 3/1988 | Granek et al. |
| 4,763,660 | A | 8/1988 | Kroll et al. |
| 4,781,200 | A | 11/1988 | Baker |
| 4,785,822 | A | 11/1988 | Wallace |
| 4,815,964 | A | 3/1989 | Cohen et al. |
| 4,850,356 | A | 7/1989 | Heath |
| 4,909,260 | A | 3/1990 | Salem et al. |
| 4,947,846 | A | 8/1990 | Kitagawa et al. |
| 4,957,109 | A | 9/1990 | Groeger et al. |
| 5,080,604 | A | 1/1992 | Rider et al. |
| 5,083,238 | A | 1/1992 | Bousman |
| 5,083,933 | A | 1/1992 | Colleran et al. |
| 5,104,253 | A | 4/1992 | Zielinski et al. |
| 5,104,334 | A | 4/1992 | Honma et al. |
| 5,131,854 | A | 7/1992 | Jose et al. |
| 5,137,466 | A | 8/1992 | Endo et al. |
| 5,154,646 | A | 10/1992 | Shoup |
| 5,158,469 | A | 10/1992 | Martin |
| 5,160,276 | A | 11/1992 | Marsh et al. |
| 5,173,059 | A | 12/1992 | Sato et al. |
| 5,176,343 | A | 1/1993 | Cheney et al. |
| 5,178,556 | A | 1/1993 | Chen |
| 5,180,312 | A | 1/1993 | Martin |
| 5,190,467 | A | 3/1993 | Ohta |
| 5,192,226 | A | 3/1993 | Wang |
| 5,197,901 | A | 3/1993 | Hashiguchi |
| 5,199,897 | A | 4/1993 | Hashiguchi |
| 5,201,669 | A | 4/1993 | Lin |
| 5,203,715 | A | 4/1993 | Yamamoto |
| 5,203,719 | A | 4/1993 | Kozono |
| 5,207,594 | A | 5/1993 | Olson |
| 5,224,479 | A | 7/1993 | Sekine |
| 5,232,383 | A | 8/1993 | Barnick |
| 5,234,357 | A | 8/1993 | Yamaguchi |
| 5,243,510 | A | 9/1993 | Cheney, II |
| 5,263,481 | A | 11/1993 | Axelgaard |
| 5,276,443 | A | 1/1994 | Gates et al. |
| 5,278,759 | A | 1/1994 | Berra et al. |
| 5,279,308 | A | 1/1994 | DiSabito et al. |
| 5,293,013 | A | 3/1994 | Takahashi |
| 5,301,680 | A | 4/1994 | Rosenberg |
| 5,320,621 | A | 6/1994 | Gordon et al. |
| 5,326,272 | A | 7/1994 | Harhen et al. |
| 5,332,330 | A | 7/1994 | Kaneko |
| 5,338,219 | A | 8/1994 | Hiramoto |
| 5,341,806 | A | 8/1994 | Gadsby et al. |
| 5,341,812 | A | 8/1994 | Allaire et al. |
| 5,353,793 | A | 10/1994 | Bornn |
| 5,362,249 | A | 11/1994 | Carter |
| 5,370,116 | A | 12/1994 | Rollman et al. |
| 5,370,550 | A | 12/1994 | Alwine et al. |
| 5,373,852 | A | 12/1994 | Harrison et al. |
| 5,376,016 | A | 12/1994 | Inaba et al. |
| 5,378,168 | A | 1/1995 | Sumida |
| 5,380,223 | A | 1/1995 | Marsh et al. |
| 5,382,176 | A | 1/1995 | Norden |
| 5,383,794 | A | 1/1995 | Davis et al. |
| 5,387,116 | A | 2/1995 | Wang |
| 5,387,127 | A | 2/1995 | Wang |
| 5,399,045 | A | 3/1995 | Yoneda et al. |
| 5,405,269 | A | 4/1995 | Stupecky |
| 5,415,164 | A | 5/1995 | Faupel et al. |
| 5,427,111 | A | 6/1995 | Traub et al. |
| 5,429,526 | A | 7/1995 | Ann |
| 5,442,940 | A | 8/1995 | Secker et al. |
| 5,454,739 | A | 10/1995 | Strand |
| 5,462,448 | A | 10/1995 | Kida et al. |
| 5,486,117 | A | 1/1996 | Chang |
| 5,494,032 | A | 2/1996 | Robinson et al. |
| 5,507,290 | A | 4/1996 | Kelly et al. |
| 5,507,665 | A | 4/1996 | Oda |
| 5,507,668 | A | 4/1996 | Lambrinos et al. |
| 5,509,822 | A | 4/1996 | Negus et al. |
| 5,511,553 | A | 4/1996 | Segalowitz |
| 5,546,950 | A | 8/1996 | Schoeckert et al. |
| 5,558,535 | A | 9/1996 | Saka et al. |
| 5,564,939 | A | 10/1996 | Maitani et al. |
| 5,566,680 | A | 10/1996 | Urion et al. |
| 5,582,180 | A | 12/1996 | Manset et al. |
| 5,584,719 | A | 12/1996 | Tsuji et al. |
| 5,599,199 | A | 2/1997 | Wright |
| 5,603,632 | A | 2/1997 | Johannes et al. |
| 5,611,708 | A | 3/1997 | Mizunuma et al. |
| 5,613,870 | A | 3/1997 | Traver, Jr. |
| 5,615,674 | A | 4/1997 | Maurer |
| 5,622,168 | A | 4/1997 | Keusch et al. |
| 5,624,271 | A | 4/1997 | Childs et al. |
| 5,626,135 | A | 5/1997 | Sanfilippo |
| 5,632,274 | A | 5/1997 | Quedens et al. |
| 5,651,689 | A | 7/1997 | Plyler et al. |
| 5,653,606 | A | 8/1997 | Chrysostomou |
| 5,674,088 | A | 10/1997 | Roche et al. |
| 5,676,694 | A | 10/1997 | Boser et al. |
| 5,679,022 | A | 10/1997 | Cappa et al. |
| 5,679,029 | A | 10/1997 | Saunier et al. |
| 5,685,303 | A | 11/1997 | Rollman et al. |
| 5,694,940 | A | 12/1997 | Unger et al. |
| 5,695,355 | A | 12/1997 | Hasenfratz et al. |
| 5,702,265 | A | 12/1997 | Yamaguchi |
| 5,704,351 | A | 1/1998 | Mortara et al. |
| 5,711,684 | A | 1/1998 | Inoue et al. |
| 5,718,596 | A | 2/1998 | Inaba et al. |
| 5,724,025 | A | 3/1998 | Tavori |
| 5,724,984 | A | 3/1998 | Arnold et al. |
| 5,725,525 | A | 3/1998 | Kordis |
| 5,741,155 | A | 4/1998 | Herman |
| 5,743,859 | A | 4/1998 | Wodlinger et al. |
| 5,749,746 | A | 5/1998 | Tan et al. |
| 5,766,133 | A | 6/1998 | Faisandier |
| 5,769,650 | A | 6/1998 | Aoyama et al. |
| 5,772,591 | A | 6/1998 | Cram |
| 5,775,953 | A | 7/1998 | Yamanashi et al. |
| 5,782,647 | A | 7/1998 | Okura et al. |
| 5,782,892 | A | 7/1998 | Castle et al. |
| 5,785,664 | A | 7/1998 | Rosenberg |
| 5,788,527 | A | 8/1998 | Sanders et al. |
| 5,797,854 | A | 8/1998 | Hedgecock |
| 5,806,152 | A | 9/1998 | Saitou et al. |
| 5,813,404 | A | 9/1998 | Devlin et al. |
| 5,813,979 | A | 9/1998 | Wolfer |
| 5,827,086 | A | 10/1998 | Fukuda |
| 5,830,000 | A | 11/1998 | Shifflett et al. |
| 5,836,783 | A | 11/1998 | Morisawa et al. |
| 5,843,141 | A | 12/1998 | Bischoff et al. |
| 5,848,456 | A | 12/1998 | Sjoqvist |
| 5,865,740 | A | 2/1999 | Kelly et al. |
| 5,865,741 | A | 2/1999 | Kelly et al. |
| 5,871,451 | A | 2/1999 | Unger et al. |
| 5,873,747 | A | 2/1999 | Tsuji |
| 5,876,232 | A | 3/1999 | Matsushita et al. |
| 5,886,576 | A | 3/1999 | Carlson |
| 5,895,284 | A | 4/1999 | Kocher et al. |
| 5,904,579 | A | 5/1999 | McLean et al. |
| 5,913,834 | A | 6/1999 | Francais |
| 5,916,159 | A | 6/1999 | Kelly et al. |
| 5,931,689 | A | 8/1999 | Patel |
| 5,931,861 | A | 8/1999 | Werner et al. |
| 5,934,926 | A | 8/1999 | Gabrisko, Jr. et al. |
| 5,935,061 | A | 8/1999 | Acker et al. |
| 5,937,950 | A | 8/1999 | Adams et al. |
| 5,938,470 | A | 8/1999 | Kashiyama |
| 5,938,597 | A | 8/1999 | Stratbucker |
| 5,941,725 | A | 8/1999 | Brennan et al. |
| 5,951,316 | A | 9/1999 | Kawano et al. |
| 5,951,497 | A | 9/1999 | Wallace et al. |
| 5,964,624 | A | 10/1999 | Pernelle |
| 5,968,087 | A | 10/1999 | Hess et al. |
| 5,971,790 | A | 10/1999 | Rohde |

(56) References Cited

U.S. PATENT DOCUMENTS

| | | |
|---|---|---|
| 5,971,799 A | 10/1999 | Swade |
| 5,980,332 A | 11/1999 | Tsuji et al. |
| 5,984,717 A | 11/1999 | Lee |
| 5,984,879 A | 11/1999 | Wallace et al. |
| 5,997,334 A | 12/1999 | Goto |
| 6,006,125 A | 12/1999 | Kelly et al. |
| 6,027,359 A | 2/2000 | Aoki et al. |
| 6,032,063 A | 2/2000 | Hoar et al. |
| 6,032,064 A | 2/2000 | Devlin et al. |
| 6,036,533 A | 3/2000 | Huang |
| 6,038,479 A | 3/2000 | Werner et al. |
| 6,038,481 A | 3/2000 | Werner et al. |
| 6,044,283 A | 3/2000 | Fein et al. |
| 6,050,838 A | 4/2000 | Norizuki et al. |
| 6,055,448 A | 4/2000 | Anderson et al. |
| 6,062,902 A | 5/2000 | Buckles et al. |
| 6,066,093 A | 5/2000 | Kelly et al. |
| 6,074,234 A | 6/2000 | Hasegawa |
| 6,098,127 A | 8/2000 | Kwang |
| 6,109,948 A | 8/2000 | Kuo |
| 6,115,623 A | 9/2000 | McFee |
| 6,116,940 A | 9/2000 | Bertens et al. |
| 6,122,536 A | 9/2000 | Sun et al. |
| 6,122,544 A | 9/2000 | Organ |
| 6,129,666 A | 10/2000 | DeLuca et al. |
| 6,132,233 A | 10/2000 | Fukuda |
| 6,139,350 A | 10/2000 | Mathesius |
| 6,139,360 A | 10/2000 | Hayashi |
| 6,152,778 A | 11/2000 | Dalton |
| 6,155,864 A | 12/2000 | Yoshiura |
| 6,157,851 A | 12/2000 | Kelly et al. |
| 6,165,017 A | 12/2000 | Kuo |
| 6,168,453 B1 | 1/2001 | Kuo |
| 6,171,139 B1 | 1/2001 | Sato et al. |
| 6,177,673 B1 | 1/2001 | Blomberg et al. |
| 6,190,385 B1 | 2/2001 | Tom et al. |
| 6,203,354 B1 | 3/2001 | Kuwahara et al. |
| 6,219,568 B1 | 4/2001 | Kelly et al. |
| 6,219,569 B1 | 4/2001 | Kelly et al. |
| 6,223,088 B1 | 4/2001 | Scharnberg et al. |
| 6,231,524 B1 | 5/2001 | Wallace et al. |
| 6,232,366 B1 | 5/2001 | Wang et al. |
| 6,234,827 B1 | 5/2001 | Nishio et al. |
| 6,236,874 B1 | 5/2001 | Devlin et al. |
| 6,240,323 B1 | 5/2001 | Calenzo, Sr. et al. |
| 6,247,963 B1 | 6/2001 | Rattner |
| 6,250,955 B1 | 6/2001 | Archuleta |
| 6,254,425 B1 | 7/2001 | Shchervinsky et al. |
| 6,257,914 B1 | 7/2001 | Comerci et al. |
| 6,257,925 B1 | 7/2001 | Jones |
| 6,280,209 B1 | 8/2001 | Bassler et al. |
| 6,280,227 B1 | 8/2001 | Terada et al. |
| 6,280,243 B1 | 8/2001 | Liu et al. |
| 6,283,789 B1 | 9/2001 | Tsai |
| 6,290,530 B1 | 9/2001 | Chang |
| 6,298,255 B1 | 10/2001 | Cordero et al. |
| 6,304,783 B1 | 10/2001 | Lyster et al. |
| 6,324,432 B1 | 11/2001 | Rigaux et al. |
| 6,339,720 B1 | 1/2002 | Anzellini et al. |
| 6,340,306 B1 | 1/2002 | Daoud |
| 6,356,779 B1 | 3/2002 | Katzenmaier et al. |
| 6,358,083 B1 | 3/2002 | Kraft |
| 6,360,119 B1 | 3/2002 | Roberts |
| 6,364,685 B1 | 4/2002 | Manning |
| 6,383,010 B1 | 5/2002 | Mayo et al. |
| 6,383,011 B2 | 5/2002 | Chen |
| 6,383,036 B1 | 5/2002 | Steinhauser et al. |
| 6,386,917 B1 | 5/2002 | Sakaguchi |
| 6,393,317 B1 | 5/2002 | Fukuda |
| 6,394,953 B1 | 5/2002 | Devlin et al. |
| 6,398,575 B1 | 6/2002 | Bresson |
| 6,398,577 B1 | 6/2002 | Simmel et al. |
| 6,400,977 B1 | 6/2002 | Kelly et al. |
| 6,411,834 B1 | 6/2002 | Nagai |
| 6,413,112 B2 | 7/2002 | Semmeling et al. |
| 6,415,169 B1 | 7/2002 | Kornrumpf et al. |
| 6,419,636 B1 | 7/2002 | Young et al. |
| 6,434,410 B1 | 8/2002 | Cordero et al. |
| 6,447,170 B1 | 9/2002 | Takahashi et al. |
| 6,450,958 B1 | 9/2002 | Linkhart et al. |
| 6,453,186 B1 | 9/2002 | Lovejoy et al. |
| 6,454,577 B1 | 9/2002 | Yi |
| 6,454,590 B1 | 9/2002 | Goodrich et al. |
| 6,454,605 B1 | 9/2002 | Bassler et al. |
| 6,456,872 B1 | 9/2002 | Faisander |
| 6,461,179 B1 | 10/2002 | Sullivan et al. |
| 6,487,430 B1 | 11/2002 | Henderson et al. |
| 6,494,744 B1 | 12/2002 | Lee |
| 6,514,099 B2 | 2/2003 | Endo |
| 6,517,372 B1 | 2/2003 | Jones |
| 6,531,657 B1 | 3/2003 | Jones, Jr. et al. |
| 6,533,600 B1 | 3/2003 | Kashiyama et al. |
| 6,540,549 B2 | 4/2003 | Rupert |
| 6,551,117 B2 | 4/2003 | Poplawski et al. |
| 6,553,246 B1 | 4/2003 | Wenger |
| 6,553,250 B2 | 4/2003 | Rantala |
| 6,558,189 B2 | 5/2003 | Groebe et al. |
| 6,561,834 B2 | 5/2003 | Chen |
| 6,564,079 B1 | 5/2003 | Cory et al. |
| 6,565,388 B1 | 5/2003 | Van Woensel et al. |
| 6,567,680 B2 | 5/2003 | Swetlik et al. |
| 6,575,759 B1 | 6/2003 | Ollivier |
| 6,575,794 B1 | 6/2003 | Nakamura |
| 6,582,252 B1 | 6/2003 | Lin |
| 6,589,066 B1 | 7/2003 | Wu |
| 6,592,391 B1 | 7/2003 | Wu |
| 6,592,404 B2 | 7/2003 | Endo |
| 6,604,963 B2 | 8/2003 | Lin |
| 6,607,397 B1 | 8/2003 | Zhang et al. |
| 6,609,018 B2 | 8/2003 | Cory et al. |
| 6,609,833 B1 | 8/2003 | Miyachi et al. |
| 6,611,705 B2 | 8/2003 | Hopman et al. |
| 6,612,860 B2 | 9/2003 | Droesbeke |
| 6,619,976 B2 | 9/2003 | Huetter et al. |
| 6,619,989 B1 | 9/2003 | Yi |
| 6,623,312 B2 | 9/2003 | Merry et al. |
| 6,636,754 B1 | 10/2003 | Baura et al. |
| 6,647,286 B1 | 11/2003 | Kato et al. |
| 6,648,665 B1 | 11/2003 | Wu |
| 6,648,666 B1 | 11/2003 | Wu |
| 6,654,626 B2 | 11/2003 | Devlin et al. |
| 6,655,979 B1 | 12/2003 | Lee |
| 6,659,790 B1 | 12/2003 | Wu |
| 6,663,412 B2 | 12/2003 | Aramoto et al. |
| 6,663,419 B2 | 12/2003 | Vaden |
| 6,663,420 B1 | 12/2003 | Xiao |
| 6,663,570 B2 | 12/2003 | Mott et al. |
| 6,669,510 B2 | 12/2003 | Yamawaki et al. |
| 6,688,894 B2 | 2/2004 | Knox, Jr. et al. |
| 6,688,907 B2 | 2/2004 | Yamaoka et al. |
| 6,702,602 B2 | 3/2004 | Wu |
| 6,702,603 B2 | 3/2004 | Wu |
| 6,702,616 B1 | 3/2004 | Chang et al. |
| 6,705,880 B2 | 3/2004 | Rhude |
| 6,709,284 B1 | 3/2004 | Avlonitis |
| 6,716,165 B1 | 4/2004 | Flanders et al. |
| 6,722,912 B2 | 4/2004 | Wu |
| 6,736,650 B1 | 5/2004 | Chen |
| 6,743,053 B2 | 6/2004 | Wu |
| 6,748,797 B2 | 6/2004 | Breed et al. |
| 6,751,493 B2 | 6/2004 | Wenger |
| 6,755,689 B2 | 6/2004 | Zhang et al. |
| 6,768,921 B2 | 7/2004 | Organ et al. |
| 6,773,293 B1 | 8/2004 | Lee |
| 6,780,065 B2 | 8/2004 | Schwarz |
| 6,786,755 B2 | 9/2004 | Dambach et al. |
| 6,786,764 B2 | 9/2004 | Sivertsen |
| 6,805,579 B2 | 10/2004 | Marchand et al. |
| 6,816,744 B2 | 11/2004 | Garfield et al. |
| 6,832,928 B2 | 12/2004 | Suzuki |
| 6,837,734 B2 | 1/2005 | Ushio et al. |
| 6,847,836 B1 | 1/2005 | Sujdak |
| 6,848,926 B2 | 2/2005 | Ling et al. |
| 6,851,969 B2 | 2/2005 | Archuletta |

(56) References Cited

U.S. PATENT DOCUMENTS

| | | |
|---|---|---|
| 6,860,750 B1 | 3/2005 | Wu |
| 6,866,535 B2 | 3/2005 | Uchida |
| 6,881,098 B2 | 4/2005 | Jeansonne et al. |
| 6,891,379 B2 | 5/2005 | Kelly et al. |
| 6,913,482 B1 | 7/2005 | Wu |
| 6,939,158 B2 | 9/2005 | Moffett et al. |
| 6,939,345 B2 | 9/2005 | KenKnight et al. |
| 6,945,796 B2 | 9/2005 | Bassler et al. |
| 6,945,807 B1 | 9/2005 | Wu |
| 6,948,973 B1 | 9/2005 | Hsu et al. |
| 6,970,731 B1 | 11/2005 | Jayaraman et al. |
| 6,973,341 B2 | 12/2005 | Watson |
| 6,973,343 B2 | 12/2005 | Wenger |
| 6,980,852 B2 | 12/2005 | Jersey-Willuhn et al. |
| 6,984,143 B2 | 1/2006 | Roese |
| 6,997,733 B2 | 2/2006 | Peng |
| 7,004,787 B2 | 2/2006 | Milan |
| 7,008,255 B1 | 3/2006 | Wang |
| 7,025,618 B2 | 4/2006 | Fukuda |
| 7,025,628 B2 | 4/2006 | LaMeres et al. |
| 7,029,286 B2 | 4/2006 | Hall et al. |
| 7,033,207 B2 | 4/2006 | Nimura |
| 7,041,918 B1 | 5/2006 | Wu |
| 7,056,134 B2 | 6/2006 | Martin et al. |
| 7,056,141 B2 | 6/2006 | Moffett et al. |
| 7,081,008 B2 | 7/2006 | Tan |
| 7,085,598 B2 | 8/2006 | Sato |
| 7,104,801 B1 | 9/2006 | Brodnick et al. |
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,144,372 B2 | 12/2006 | Ng et al. |
| 7,150,655 B2 | 12/2006 | Mastrototaro et al. |
| 7,160,136 B2 | 1/2007 | Zhang et al. |
| 7,169,107 B2 | 1/2007 | Jersey-Willuhn et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,184,820 B2 | 2/2007 | Jersey-Willuhn et al. |
| 7,189,097 B2 | 3/2007 | Benham |
| 7,197,357 B2 | 3/2007 | Istvan et al. |
| 7,198,502 B2 | 4/2007 | Koenig et al. |
| 7,201,599 B2 | 4/2007 | Holub |
| 7,207,825 B2 | 4/2007 | Le Gallic et al. |
| 7,236,825 B2 | 6/2007 | Wang |
| 7,252,542 B2 | 8/2007 | Chen |
| 7,252,556 B2 | 8/2007 | Anbo et al. |
| 7,252,565 B2 | 8/2007 | Hunter |
| 7,258,566 B2 | 8/2007 | Koenig et al. |
| 7,264,510 B2 | 9/2007 | Koenig et al. |
| 7,270,568 B2 | 9/2007 | Osypka |
| 7,272,427 B2 | 9/2007 | Ristolainen |
| 7,272,428 B2 | 9/2007 | Hopman et al. |
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,319,895 B2 | 1/2008 | Klefstad-Sillinville et al. |
| 7,322,849 B2 | 1/2008 | Sutton |
| 7,322,857 B2 | 1/2008 | Chen |
| 7,329,139 B2 | 2/2008 | Benham |
| 7,333,850 B2 | 2/2008 | Marossero et al. |
| 7,347,710 B2 | 3/2008 | Ohtaka et al. |
| 7,347,826 B1 | 3/2008 | Karicherla et al. |
| 7,359,751 B1 | 4/2008 | Erickson et al. |
| 7,361,058 B1 | 4/2008 | Lien et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodemann et al. |
| 7,396,246 B2 | 7/2008 | Okada et al. |
| 7,399,195 B2 | 7/2008 | Kim et al. |
| 7,401,946 B2 | 7/2008 | Laukhuf |
| 7,402,071 B2 | 7/2008 | Ohtaka et al. |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achtner et al. |
| 7,462,074 B1 | 12/2008 | Devlin et al. |
| 7,465,187 B1 | 12/2008 | Wu |
| 7,473,141 B2 | 1/2009 | Liao |
| 7,488,187 B2 | 2/2009 | Wolf |
| 7,494,383 B2 | 2/2009 | Cohen et al. |
| 7,497,738 B2 | 3/2009 | Kuo |
| 7,503,807 B2 | 3/2009 | Martin et al. |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,604,511 B1 | 10/2009 | Johnson |
| 7,618,377 B2 | 11/2009 | McAtamney et al. |
| 7,632,130 B2 | 12/2009 | Sami |
| 7,666,028 B2 | 2/2010 | Meleck |
| 7,826,882 B2 | 11/2010 | McIntire et al. |
| 8,038,484 B2 | 10/2011 | Selvitelli et al. |
| 8,109,883 B2 | 2/2012 | Meyer et al. |
| 8,255,041 B2 | 8/2012 | Istvan et al. |
| 8,568,160 B2 | 10/2013 | Coggins et al. |
| 2002/0133069 A1 | 9/2002 | Roberts |
| 2002/0138011 A1 | 9/2002 | Rantala |
| 2002/0188216 A1 | 12/2002 | Kayyali et al. |
| 2003/0068914 A1 | 4/2003 | Merry et al. |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2005/0164551 A1 | 7/2005 | Wlos |
| 2005/0177052 A1 | 8/2005 | Istvan et al. |
| 2005/0182466 A1 | 8/2005 | Mahajan |
| 2005/0203349 A1 | 9/2005 | Nanikashvili |
| 2006/0073728 A1 | 4/2006 | Zaiken et al. |
| 2006/0286861 A1 | 12/2006 | Avevor et al. |
| 2007/0038057 A1 | 2/2007 | Nam et al. |
| 2007/0260133 A1 | 11/2007 | Meyer |
| 2008/0132106 A1 | 6/2008 | Burnes et al. |
| 2009/0099423 A1 | 4/2009 | Al-Ali et al. |
| 2011/0092833 A1 | 4/2011 | Farrior |
| 2013/0303927 A1 | 11/2013 | Burnes et al. |

FOREIGN PATENT DOCUMENTS

| | | |
|---|---|---|
| DE | 102004032410 | 1/2006 |
| EP | 0 766 946 | 4/1997 |
| EP | 0 799 628 | 10/1997 |
| EP | 1 050 269 | 11/2000 |
| EP | 1 932 470 | 6/2008 |
| EP | 2 070 474 | 6/2009 |
| JP | 1-42055 | 12/1989 |
| JP | 3-13830 | 3/1991 |
| JP | 2007-163528 | 6/1995 |
| JP | 11-318921 | 11/1999 |
| JP | 2001-189629 | 7/2001 |
| JP | 2003/010138 | 1/2003 |
| JP | 2004/282608 | 10/2004 |
| WO | WO 03/028550 | 4/2003 |
| WO | WO 03 047 427 | 6/2003 |
| WO | WO 2008/092098 | 7/2008 |

OTHER PUBLICATIONS

International Search Report EP 07 251 765 dated Mar. 31, 2008.
International Search Report EP 07 254 691 dated Mar. 25, 2008.
International Search Report EP 08 164 409 dated Jan. 27, 2009.
European Search Report EP 07 254 691 dated Mar. 25, 2008.
International Search Report corresponding to European Appl. No. EP 10 01 3624.1; date of completion was Mar. 24, 2011; date of mailing was Apr. 4, 2011.

(56) References Cited

OTHER PUBLICATIONS

European Office Action dated Dec. 20, 2011 for European Patent Appln. No. EP 07 253 850.7.
International Search Report EP07253850 dated Dec. 21, 2007.
Andreas Boos et al.; "A New Lightweight Fetal Telemetry System"; Dec. 1995; Hewlett-Packard Journal; pp. 82-93.
European Search Report for EP 11 00 6002 dated Nov. 15, 2011.
U.S. Appl. No. 14/044,932, Oct. 3, 2013, Coggins, et al.
Communication pursuant to Article 94(3) EPC for European Patent Application No. 07 253 850.7-2319 dated Dec. 20, 2011, 5 pages.
Response to Communication pursuant to Article 94(3) EPC for European Patent Application No. 07 253 850.7-2319 dated Dec. 20, 2011 filed on Jun. 29, 2012, 3 pages.
Notice of Reasons for Rejection for Japanese Patent Application No. 2007-254792 dated Feb. 8, 2013, 5 pages, (with English translation).
Notice of Allowance for Japanese Patent Application No. 2007-254792 dated Jan. 29, 2014, 3 pages.
Office Action dated Mar. 8, 2013 for Mexican Application No. MX/a/2007/012064, filed Sep. 28, 2007, 4 pages.
Examiner's First Report on Australian Patent Application No. 2007237339 dated May 23, 2012, 4 pages.
Response to Examiner's Report dated May 23, 2012 for Australian Patent Application No. 2007237339 filed Jan. 29, 2013, 12 pages.
Patent Examination Report No. 2 for Australian Patent Application No. 2007237339 dated Mar. 15, 2013, 5 pages.
Notice of Allowance for Australian Patent Application No. 2007237339 dated Nov. 28, 2013, 2 pages.
Chinese Office Action for Chinese Patent Application No. 200710300791.X dated Dec. 6, 2010, 14 pages, (with English translation).
Notification of the Second Office Action for Chinese Patent Application No. 200710300791.X dated Aug. 24, 2011, 8 pages, (with English translation).
EP Search Report dated Mar. 25, 2008 for European Patent Application No. 07 254 691.4-1265 dated Mar. 25, 2008, 6 pages.
Communication pursuant to Article 94(3) EPC for European Patent Application No. 07 254 691.4-1265 dated Nov. 24, 2010, 4 pages.
Response to Communication Pursuant to Article 94(3) dated Nov. 24, 2010 for European Patent Application No. 07254691.4 filed on Mar. 30, 2011, 3 pages.
Communication Pursuant to Article 94(3) EPC dated Aug. 13, 2013, for European Appl. No. 07 254 691.4, 5 pages.
Response to Communication Pursuant to Article 94(3) EPC dated Aug. 13, 2013, for European Appl. No. 07 254 691.4response dated Jan. 21, 2014, 2 pages.
Notice of Reasons for Rejection for Japanese Patent Application No. 2007-314074 dated Oct. 16, 2012, 4 pages, (English translation only).
Mexican Office Action for Mexican Patent Application No. MX/a/2007/015295 dated Mar. 8, 2013, 3 pages, (English translation only).
Response to Office Action for Mexican Patent Application No. MX/a/2007/015295 dated Mar. 8, 2013, response dated Apr. 19, 2013, 9 pages.
Notice of Allowance of Mexican Patent Application No. MX/a/2007/015295 dated Jun. 26, 2013, 2 pages.
Examination Report No. 1 dated Sep. 3, 2013 for Australian Application No. 2011204993 filed Jul. 26, 2012, 3 pages.
Response to Examination Report No. 1 dated Sep. 3, 2013 for Australian Application No. 2011204993 filed Jul. 26, 2012, response dated Dec. 23, 2013, 15 pages.
Response to Chinese Office Action in Chinese Application No. 201010624971.5 filed on May 4, 2011, 21 pages.
Notification of Entry into Examination Procedure for Chinese Patent Application No. 201010624971.5 dated Oct. 11, 2012, 2 pages, (with English translation).
Office Action dated Nov. 28, 2013 for Chinese Patent Application No. 201010624971.5, 24 ppages, (with English translation).
Extended European Search Report for European Patent Application No. 10013624.1-2319/2314215 dated Apr. 4, 2011, 14 pages.
Response to Communication dated May 10, 2011 in European Patent Application No. 10013624.1-2319/2314215 filed on Nov. 2, 2011, 5 pages.
Examination Report Action dated Nov. 12, 2013 in European Patent Application No. 10013624.1-2319/2314215 filed on Nov. 2, 2011, 6 pages.
Response to European Search Report for European Application No. 1100600237-1526 filed Jul. 31, 2012, 6 pages.
U.S Appl. No. 11/633,709, filed Dec. 5, 2006.
U.S. Appl. No. 11/528,914, filed Sep. 8, 2009.
U.S. Appl. No. 12/876,316, filed Sep. 7, 2010.
Patent No. 8,568,160, issued Oct. 29, 2013.

CABLE MONITORING APPARATUS

RELATED APPLICATIONS

This application is a divisional application under 35 U.S.C 121 of and claims priority to co-pending U.S. application Ser. No. 11/528,914 filed Sep. 28, 2006 entitled "CABLE MONITORING APPARTUS" which is incorporated by reference in its entirety for all purposes.

BACKGROUND

1. Technical Field

The present disclosure relates to medical equipment. In particular, the present disclosure relates to a cable monitoring apparatus which checks the functionality of an electrical cable adapted to connect to a medical apparatus, such as a fetal monitor.

2. Description of Related Art

Fetal monitors have been widely used and are capable of measuring a wide variety of uterine, fetal and maternal parameters, such as for example, uterine temperature, intrauterine pressure, fetal electrocardiogram, etc. This information may be gathered via a variety of sensors (e.g., electrode arrays, pressure transducers, catheters, etc.) applied to the maternal patient. Monitoring signals, from the fetus and maternal patient, are received by the sensors, transmitted via electrical cables to a fetal monitor and displayed on the fetal monitor.

Typically, during labor and delivery, a multitude of sensors are required to receive monitoring signals containing maternal and fetal information. Application of maternal and fetal sensors is time consuming and at times unpleasant to the woman, particularly the application of invasive devices such as an intrauterine pressure transducer or a fetal scalp electrode. The proper operation of sensors is essential and clinicians continually monitor the various sensors and the associated systems to check functionality and to insure the sensors are providing accurate information.

When a sensor is not functioning properly or not providing accurate information, it becomes necessary to troubleshoot the entire fetal monitoring system to determine the origin of the malfunction. One troubleshooting step includes determining if the origin of the malfunction is hardware related, in particular a faulty sensor and/or electrical cable. Typically, electrical cables are easier to diagnose and replace since electrical cable replacement usually does not require the removal and reapplication of the sensor. Reusable cables may cost much more than disposable sensors, making the potentially unnecessary replacement of cables wasteful. Therefore, there is a need for a cable monitoring apparatus for determining whether the fetal monitoring cables are functioning properly.

SUMMARY

The present disclosure relates to medical equipment. In particular, the present disclosure relates to a cable monitoring apparatus which checks the functionality of an electrical cable adapted to connect to a medical apparatus, such as a fetal monitor, as well as allows for zeroing and/or re-zeroing of monitoring functions of the medical apparatus, wherein monitoring signals are supplied from fetal and maternal monitoring sensors.

In accordance with one preferred embodiment, a cable monitoring apparatus includes a housing having an input interface, adapted to electrically connect to one end of a medical cable, and an output interface adapted to electrically connect to an electrical system. Signal processing circuitry is incorporated within the housing for receiving a medical signal from the medical cable via the input interface and for selectively passing the medical signal to the electrical system via the output interface when in a first mode of operation, and has application software for selectively testing the functionality of the medical cable when in a second mode of operation. The medical signal may include at least one monitoring signal selected from a group consisting of fetal and maternal medical signals. Preferably, the at least one monitoring signal is generated from a medical device selected from a group consisting of at least one medical electrode, a medical electrode sensor array, an abdominal strain gauge, a tocodynamometer, an intrauterine pressure catheter, an ultrasound transducer, a vacuum pressure sensor, a pulse oximeter, a pH sensor, a cervical dilation sensor, a cervical effacement sensor, a cervical length sensor, a fetal station sensor, and an ultrasound transducer.

The housing may include a cable diagnostic interface adapted to electrically connect with the remaining end of the medical cable whereby the software of the signal processing circuitry tests the functionality of the medical cable when in the second mode of operation. The housing includes at least one indicator for indicating an operating parameter corresponding to functionality of the medical cable. The housing may include first and second input interfaces for electrical connection to respective first and second medical cables.

The signal processing circuitry may be adapted to process the at least one monitoring signal when in the first mode of operation and provide an output signal indicative of an operating parameter of the at least one monitoring signal. The output signal may correspond to one of uterine activity or ECG activity. The housing may also include an output signal indicator associated with the output signal for displaying a condition of the output signal. The output signal indicator may be one of a visual or an audible alarm.

The signal processing circuitry may be further configured to perform a zero/re-zero function wherein the at least one monitoring signal is short-circuited to create a zero voltage signal. The signal processing circuitry is adapted to short circuit the at least one monitoring signal for a predetermined period of time. An indicator may be provided for indicating that the at least one monitoring signal is short-circuited.

Alternatively, a signature signal transmitter may be adapted to transmit a signature signal through the medical cable to a patient. The signature signal may be identifiable by the signal processing circuitry to determine the functionality of the medical cable.

In accordance with another embodiment, a cable monitoring system includes a cable monitor operable between a first and a second mode of operation wherein the first mode of operation selectively passes at least one monitoring signal from a medical device to a monitoring apparatus, and wherein the second mode of operation determines the functionality of an electrical cable. The at least one monitoring signal may be selected from a group consisting of fetal and maternal medical signals. A first input receives the at least one monitoring signal and a first output selectively passes the at least one monitoring signal to the monitoring apparatus. A diagnostic input may be provided whereby, in the second mode of operation, one end of the medical cable is connected to the first input and a second end of the medical cable is connected to the diagnostic input to thereby determine the functionality of the electrical cable. Signal processing circuitry is adapted to selectively pass the at least one monitoring signal from the medical device to the monitoring apparatus and to determine the functionality of the electrical cable.

In accordance with another embodiment, a method for fetal monitoring is disclosed. A medical cable monitor is electrically connecting with a fetal monitoring apparatus. One end of a medical cable is electrically connecting to an input interface of the medical cable monitor. In one mode of operation, the other end of the medical cable is electrically connected to a cable diagnostic interface of the cable monitor. In this mode of operation, signal processing circuitry of the medical cable monitor tests the functionality of the medical cable connected between the input interface and the cable diagnostic interface. In another mode of operation one end of medical cable is electrically connected to a sensor. The sensor senses maternal or fetal parameters and sends a maternal or fetal monitoring signal associated with the maternal or fetal parameters to the input of the medical cable monitor. Signal processing circuitry of the medical cable monitor passes the fetal monitoring signal to the fetal monitor.

In the step of connecting one end of the medical cable to a sensor, a sensor is selected from a group consisting of a medical electrode, a medical electrode sensor array, an abdominal strain gauge, a tocodynamometer, an intrauterine pressure catheter, a vacuum pressure sensor, a pulse oximeter, a pH sensor, a cervical dilation sensor, a cervical effacement sensor, a cervical length sensor, a fetal station sensor, and an ultrasound transducer.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

Figure 1:
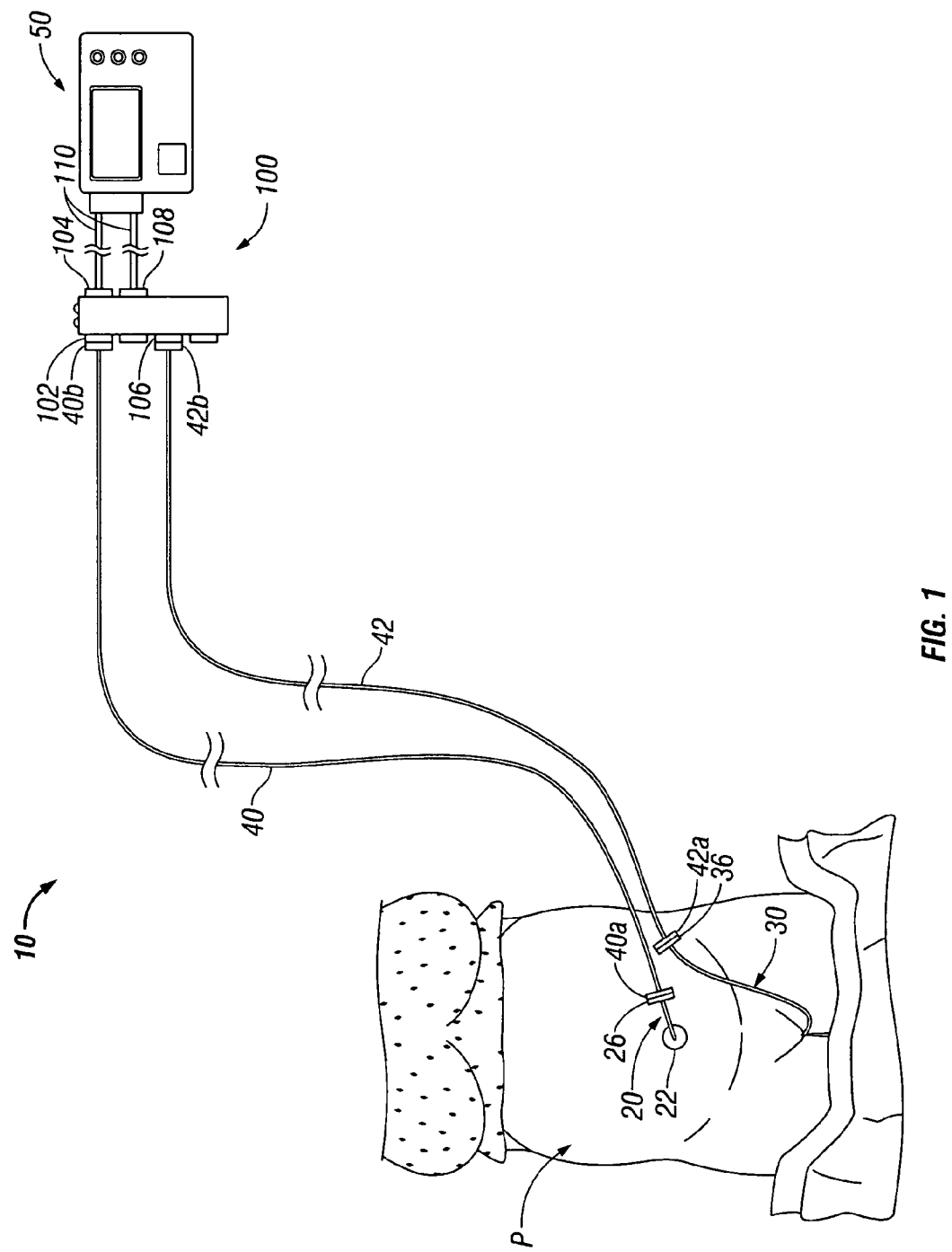
FIG. 1 is a view of a fetal monitoring system incorporating a cable monitoring apparatus in accordance with the present disclosure.

FIG. 1 shows a fetal monitoring system 10 incorporating a cable monitoring apparatus according to the present disclosure. The fetal monitoring system 10 includes one or more sensor, devices or probes, such as fetal electrocardiogram (FECG) sensor 20 and an intrauterine pressure (IUP) catheter 30. The FECG sensor 20 may include at least one electrode adapted to adhere to skin on the abdomen of the patient P. The IUP catheter 30 may be a pressure catheter placed within the uterus of the patient P. The FECG sensor 20 and the IUP catheter 30 are operably and electrically coupled with the FECG sensor cable connector 26 and IUP catheter cable connector 36, respectively.

In the discussion which follows, the term cable may incorporate a single conductor or may comprise an assembly of conductors arranged in any mode of operation known in the art. Connector refers to a single plug, receptacle, or other device capable of electro-mechanically connecting to a cable, device or apparatus. A connector assembly refers to the connection between two connectors wherein the connectors facilitate connectivity between two cables, devices or apparatus, or any combination thereof. Connection between the two components may be solely electrical without any mechanical means of connection. Such electrical connection may be infrared or incorporate electromagnetic wave principles. Thus, the term "connection" or "electrical connection" is to be construed as any electrical, mechanical connection or combination thereof known in the art.

The FECG electrical cable 40 and the IUP electrical cable 42 first connectors 40A, 42A are connected to the respective device connectors 26, 36. In the prior art, second connectors 40B, 42B of the cables 40, 42 connect directly to the monitoring device 50. Signal loss at the monitoring device 50 typically resulted in the replacement of an electrical cable 40, 42 since cable replacement is easier than the removal and subsequent reapplication of a sensor 20,30.

The first embodiment of a cable monitoring apparatus 100 in accordance with the present disclosure will now be discussed. Cable monitoring apparatus 100 is coupled between one or more electrical cables 40, 42 and the monitoring device 50. The FECG electrical cable second connector 40B of the FECG sensor cable 40 electro-mechanically connects to the first input connector 102 and the sensed information from the FECG sensor 20 is selectively passed through the first output connector 104 to the monitoring device 50. The IUP sensor cable second connector 42B of the IUP sensor cable 42 electro-mechanically connects to the second input connector 106 and the sensed information from the IUP sensor 30 is selectively passed through the second output connector 108 to a monitoring device 50. Cable monitoring apparatus 100 electro-mechanically connects to the monitoring device 50 with two interface cables 110. It is envisioned that the cable monitoring apparatus 100 electro-mechanically connects to the monitoring device in any number of ways known in the art.

FIG. 1 illustrates a fetal monitoring system 10 with a cable monitoring apparatus 100 interfacing with two sensor cables 40, 42 and one monitoring device 50. Monitoring device 50 may be a fetal monitoring device or any other device capable of receiving and displaying a monitoring signal. The present disclosure may interface with any number of cables or monitoring devices.

In a first mode of operation of cable monitoring apparatus 100, sensed information is passed from the sensors 20, 30 through the cables 40, 42 and the cable monitoring apparatus 100 and to the monitoring device 50. In a first mode of operation, cable monitoring apparatus 100 does not substantially alter or degrade the signal provided to the fetal monitoring system 10.

Figure 2:
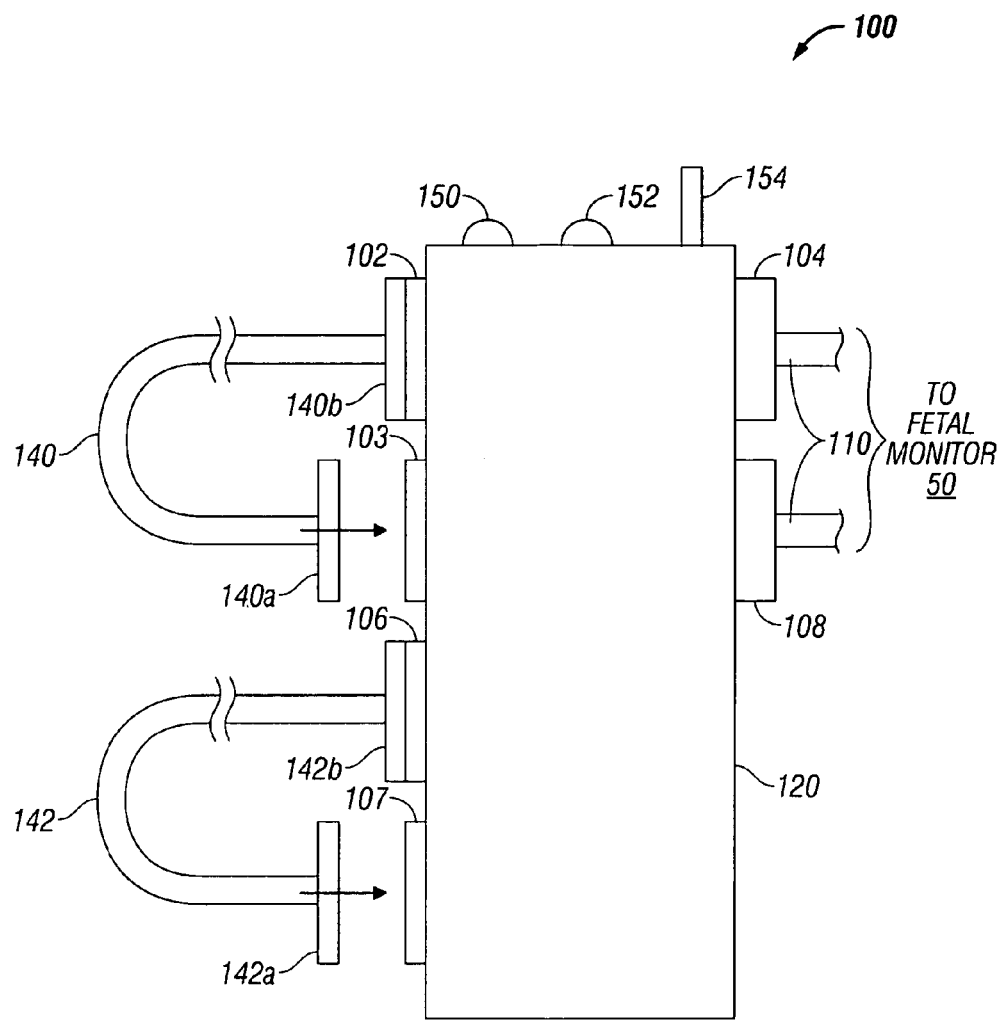
FIG. 2. is a view of the cable monitoring apparatus of FIG. 1.

With reference to FIG. 2, cable monitoring apparatus 100 consists of a housing 120 which houses a plurality of connectors and user interface devices described hereinbelow. In this particular embodiment, cable monitoring apparatus 100 is configured to connect to two medical sensors although it is envisioned cable monitoring apparatus 100 described herein may connect to any number of medical sensors or devices. Housing 120 may be sufficiently small and manufactured from lightweight materials, such as plastic, such that the cable monitoring apparatus 100 is a light-weight inline device.

FIG. 2 illustrates the cable monitoring apparatus 100 in a second mode of operation wherein cable monitoring apparatus 100 is utilized in a diagnostic capacity. Clinicians start the process of troubleshooting after it is determined that the fetal monitoring system 10 is not operating correctly. The cable monitoring apparatus 100 may be used as a diagnostic tool to determine the functionality of electrical cables 140, 142. The cable monitoring apparatus 100 may perform a number of diagnostic tests known in the art.

Second connector 140B of an electrical cable 140 is electro-mechanically connected to the first input connector 102. The first connector 140A of the same electrical cable 140 is disconnected from a medical sensor and electro-mechanically connected to the first diagnostic connector 103. A second electrical cable 142 may connect in a similar fashion with the second connector 142B connected to a second input connector 106 and the first connector 142A connected to a second diagnostic connector 107. The various electrical cables 140, 142 attached to the cable monitoring apparatus 100 may operate independent of each other wherein an electrical cable may be arranged in the first mode of operation while a second electrical cable may be arranged in the second mode of operation.

With reference to FIGS. 1 and 2, switching from the first mode of operation, as shown in FIG. 1 wherein sensed information is selectively passed through the cable monitoring apparatus, to the second mode of operation, as shown in FIG. 2 wherein the cable monitoring apparatus is used to diagnose an electrical cable, requires disconnecting the first connectors 140A, 142A of the first and second electrical cables 40, 42 from the FECG sensor cable connector 26 and the IUP catheter cable connector 36 and reconnecting the first connectors 140A, 142A to the first and second diagnostic connectors 103, 107.

Alternatively, the clinician may diagnose the electrical cable with cable monitoring apparatus 100 prior to connecting the first connectors 140A, 142A to the sensors connectors 26, 36.

Returning to FIG. 2, first cable indicator 150 indicates the functionality of a cable connected between the first input connector 102 and the first diagnostic connector 103. Second cable indicator 152 indicates the functionality of a cable connected between the second input connector 106 and the second diagnostic connector 107. First and second cable indicators 150, 152 may be audio indicators, visual indicators, or any indicator known in the art, or combination thereof.

Figure 3:
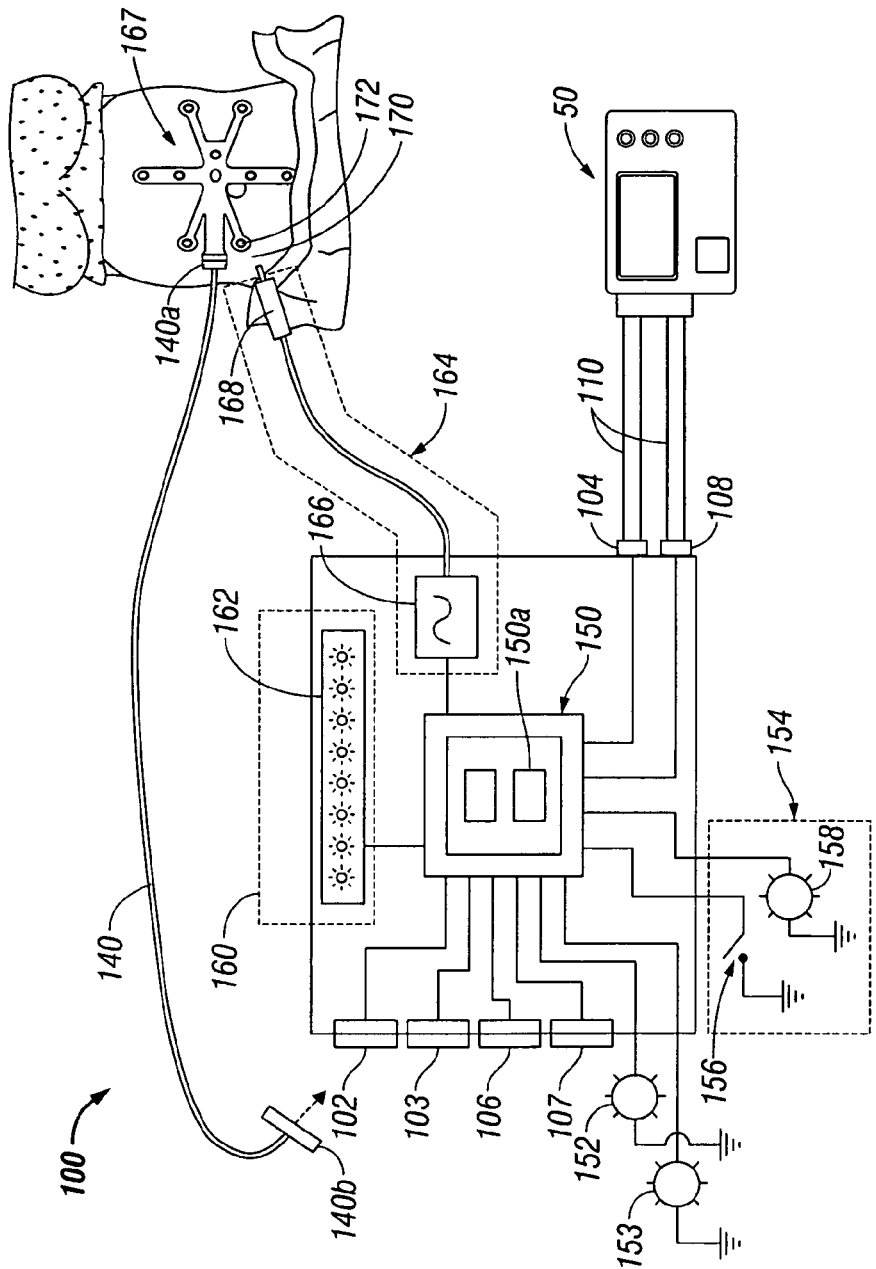
FIG. 3 is an electrical schematic illustrating the components of the cable monitoring apparatus.

FIG. 3 is a schematic of the cable monitoring apparatus 100 including signal processing circuitry 150 operably coupled to the various input connectors, output connectors, test connectors and indicator devices described hereinbelow. Signal processing circuitry 150 may include a Digital Signal Processor (DSP) 150A having a memory storing a set of programmable instructions capable of being executed by the DSP 150A for performing the functions described herein. Signal processing circuitry 150 may be an application-specific integrated circuit (ASIC) customized for this particular use or may be a general purpose device adapted for this use.

In the first mode of operation, signal processing circuitry 150 selectively passes monitoring information from the first and second input connectors 102, 106 to the respective first and second output connectors 104, 108. First and second output connectors 104, 108 pass monitoring information to display monitor 50. In this mode of operation, the monitoring information received at the display monitor 50 is essentially identical to the monitoring information received by the sensors 20, 30.

In the second mode of operation, signal processing circuitry 150 performs a diagnostic check on an electrical cable attached between the first or second input connectors 102, 106 and the respective first or second diagnostic connectors 103, 107. Signal processing circuitry 150 is connected to various indicators 152, 153 to indicate the results of the diagnostic check for each electrical cable. Diagnostic check may include testing the continuity and impedance of the various conductors, testing continuity and impedance between the various conductors, testing the capacitive properties of the cable, testing the insulation in the cable, measuring losses within the cable and conductors, measuring the frequency response and signal losses at various frequencies and any other test known in the art. Various indicators 152, 153 are indicative of at least one operating feature of the electrical cable which include test performed, or measurements made, on the cable. Indicators 152, 153 may be audible indicators, visual indicators, or other indicators known in the art.

The first or second input connectors 102, 106 may interface with various medical sensors (not shown) including a medical electrode, a medical electrode sensor array, an abdominal strain gage, a tocodynamometer, an intrauterine pressure catheter, and an ultrasound transducer.

One such sensor, the pressure catheter, is a common apparatus for measuring the uterine contractions of a maternal abdomen. Various pressure catheter components and systems are described in U.S. Pat. No. 5,566,680 to Urion et al. titled "Transducer-Tipped Intrauterine Pressure Catheter System", the contents of which are incorporated herein by reference. Referring to FIG. 1, the IUP catheter 30 is a type of pressure catheter that measures force applied to the pressure catheter by the patient P.

In monitoring fetal contractions with a pressure catheter it often becomes necessary or desirable to "zero" or "re-zero" the pressure catheter in situ. U.S. application Ser. No. 10/952, 942 to Zaiken et al. titled "Intrauterine Pressure Catheter Interface Cable System", the contents of which are incorporated herein by reference, describes a pressure catheter and a zero/re-zero apparatus and method.

Referring again to FIG. 3, an alternative embodiment of the present disclosure includes zero/re-zero hardware 154. The signal processing circuitry 150 of the cable monitoring apparatus is operably connected to zero/re-zero selector 156 and zero/re-zero indicator 158. Clinicians initiate a zero/re-zero of the monitoring device 50 and the pressure catheter by depressing the zero/re-zero selector 156. The signal processing circuitry 150 short-circuits the output connector, corresponding to the pressure catheter, to ground thus creating a zero voltage signal to the monitoring device 50. The zero voltage signal is held for a predetermined period of time and clinicians are alerted that the output connector is short-circuited by a zero/re-zero indicator 158. The length of time the zero voltage signal is held must be sufficient for clinician to perform a zero/re-zero operation on the monitoring device 50, typically between 5 and 30 seconds.

In yet another embodiment, the cable monitoring apparatus includes an indicator circuit 160. At least one indicator 162, corresponding to a medical signal received by a input connector 102, 106, provides information about an operating feature of the medical signal. Indicators may identify the presence of uterine or fetal ECG activity Referring again to FIG. 3, indicators 162 may correspond to the number of electrodes on the electrode array 167 applied to the maternal abdomen 170. Indicator circuit 160 is operably connected to the signal processing circuitry 150 and the signal processing circuitry 150 may drive the indicators 162 with a signal indicative of at least one operating feature of the electrical cable 140. An operating feature of the electrical cable 140 may be associated with the functionality of the cable, the quality of the signal transmitted by the electrical cable, or a feature of the electrical cable or medical signal.

In yet another embodiment of the present disclosure, indicators 162 include lights driven by signals from the signal processing circuitry 150 wherein the signals are indicative of the functionality of an electrical cable. Indicator circuit 160 includes an array of indicator lights 162 with at least one indicator light corresponding to a medical sensor. Each individual indicator light may be driven with a signal proportional to the medical signal from the sensor or device. Clinicians can troubleshoot problems with an electrical cable 140, sensor or device containing sensors, such as an electrode array 167, by observing the array of indicator lights 162 on the cable monitoring apparatus 100.

Referring again to FIG. 3, in yet another embodiment, the cable monitoring apparatus includes a signal transmitter assembly 164 having a signal generator 166 and a signal applicator 168. Signal generator 166 generates and supplies a signature signal to the signal processing circuitry 150 and the signal applicator 168. The signature signal is a low energy signal with distinct and identifiable voltage and frequency characteristics. The signal applicator 168 is applied to patient skin 170 in close proximity to a medical device, such as an electrode 172 in an electrode array 167. Electrode 172 receives the signature signal and supplies the sensed information, including the signature signal, to the cable monitoring apparatus 100 through the electrical cable 140. The signal processing circuitry 150 receives the sensed information, including the signature signal, and processes the sensed information and signature signal. The DSP 150A of the signal processing circuit 150 may compare the received signature signal to the generated signature signal to determine the functionality of the circuit between the signal applicator 168 and the cable monitoring apparatus 100. Various factors which may affect the circuit include the conductivity of patient skin 170 adjacent the electrode, the connection between patient skin 170 and the electrode 172, the electrical cable 140 and the electrical cable connections 140A, 140B.

In yet another embodiment, the signal applicator 168 is integrated into the electrode array 167. In use, signature signal is transmitted on one conductor of electrical cable 140, applied to patient skin 170 by the signal applicator integrated into the electrode array and received by the plurality of electrodes 172 on the electrode array 167. The DSP 150A of the signal processing circuit 150 may compare the received signal to the generated signal to determine the functionality of the electrode array 167 and electrical cable 140. In the case where all electrodes are receiving a signature signal of poor quality DSP 150A may compare the plurality of received signals to determine if the poor signal is due to the signal applicator.

Figure 4:
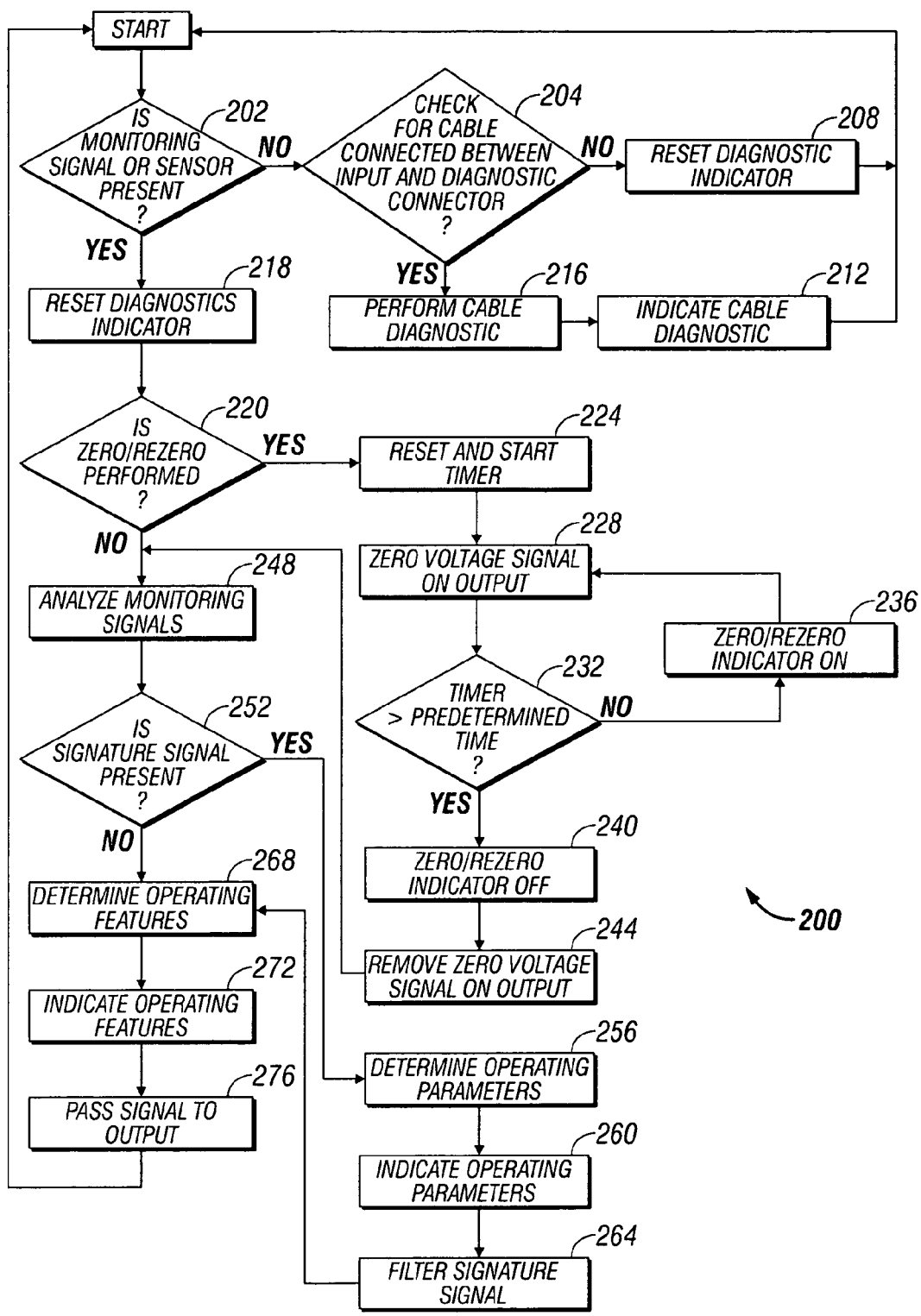
FIG. 4 is a programming flowchart illustrating functionality of the cable monitoring apparatus.

Referring now to FIG. 4, programming flowchart 200 illustrates processes executed by the DSP 150A for performing the functions described herein in accordance with the present disclosure. Cable monitoring apparatus may be configured in a first or second mode of operation prior to executing the steps and the mode of operation and connections may be modified at any time. While the programming flowchart of FIG. 4 includes multiple embodiments of the present disclosure, the steps executed by the DSP 150A may be limited to one or more of the various embodiment described herein.

Step 202 determines if a monitoring signal or sensor is present on an input connector. Various methods of detecting the presence of an input connector may be used such as measuring the impedance of the input or by analyzing the input signal. Sensors may also exhibit a distinct impedance characteristic or may contain a specific identification feature, such as a fixed resistor. Step 204 is executed if the signal or device is not detected on the input.

Step 204 checks for a cable connected between a input connector and a corresponding diagnostic connector. The presence of a cable between a input connector and a diagnostic connector may be determined by checking continuity, by a sensor detecting the physical presence of a cable or by user input. Step 208, which resets the diagnostic indicator, is executed if a cable is not detected between the input connectors. Step 216, which is executed if a cable is detected, performs cable diagnostic and the results of the diagnostics are indicated in Step 212.

Returning to Step 202, if a signal is detected on the input, the diagnostics indicator is reset in Step 218. The next step in sequence, Step 220, determines if the user has initiated a zero/re-zero function.

Zero/re-zero function is executed by Steps 224, 228, 232 and 236. Step 224 resets and starts the zero/re-zero timer. A zero voltage signal is held on the output in Step 228. If the zero/re-zero timer, in Step 232, has not exceeded the pre-determined time, the zero/re-zero indicator is turned on in Step 236, and the zero voltage signal is maintained on the output in Step 228. When the zero/re-zero timer exceeds the pre-determined time, the zero/re-zero indicator is turned off in Step 240, and the zero voltage signal is removed from the output in Step 244.

Returning to Step 220, if a zero/re-zero function is not performed, the monitoring signal at the input is analyzed in Step 248. The next step in the sequence, Step 252, checks for the presence of a signature signal in the monitoring signal. The clinician applies the signature signal transmitter to the patient (not shown in flow chart), in close proximity to the sensor, or to the sensor itself, in order to either check the functionality of the electrical cables and/or the electrical circuits. If the signature signal is present, Step 256 determines various cable and circuit parameters by comparing the received signature signal to the generated signature signal. Step 260 indicates at least one parameters indicative of the functionality of the electrical cable or circuit. Step 264 selectively filters the medical signal and removes at least a portion of the signature signal from the medical signal.

Next, in Step 268, the medical signal is analyzed to determine one or more operating features of the medical signal. At least one operating feature is indicated in Step 272 and the medical signal is passed to the output in Step 276.

In yet another embodiment, the features, functions and methods of the present disclosure, are incorporated into another electronic device, such as a personal computer, oscilloscope or monitoring device.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A method for monitoring a parameter associated with labor, comprising:

electrically connecting a medical cable monitor with a monitoring apparatus;

electrically connecting a first end of a medical cable to an input interface of the medical cable monitor and a second end of the medical cable to a cable diagnostic interface of the medical cable monitor;

activating the medical cable monitor in one mode of operation whereby signal processing circuitry of the medical cable monitor tests functionality of the medical cable connected between the input interface and the cable diagnostic interface;

electrically connecting the second end of the medical cable to a sensor positioned adjacent a subject;

sensing a parameter with the sensor and sending a monitoring signal associated with the parameter to the input interface of the cable monitor; and activating the cable monitor in another mode of operation whereby the signal processing circuitry passes the monitoring signal to the monitoring apparatus.

2. The method according to claim 1 wherein sensing a parameter with the sensor comprises sensing one of a fetal or maternal parameter.

3. The method according to claim 2 wherein electrically connecting the second end of the medical cable to a sensor comprises connecting the medical cable to a sensor selected from the group consisting of at least one medical electrode, a medical electrode sensor array, an abdominal strain gauge, a tocodynamometer, an intrauterine pressure catheter, and an ultrasound transducer.

4. The method according to claim 2 wherein the electrically connecting the second end of the medical cable to a sensor comprises connecting the medical cable to a vacuum pressure sensor.

5. The method according to claim 2 wherein electrically connecting the second end of the medical cable to a sensor comprises connecting the medical cable to a pulse oximeter.

6. The method according to claim 2 wherein electrically connecting the second end of the medical cable to a sensor comprises connecting the medical cable to a pH sensing device.

7. The method according to claim 2 wherein electrically connecting the second end of the medical cable to a sensor comprises connecting the medical cable to a sensor selected from a group consisting of a cervical dilation sensor, a cervical effacement sensor and a cervical length sensor.

8. The method according to claim 2 wherein electrically connecting the second end of the medical cable to a sensor comprises connecting the medical cable to a fetal station sensor.

9. The method according to claim 2 further comprising:
electrically connecting a first end of a second medical cable to a second input interface of the medical cable monitor and a second end of the second medical cable to a second cable diagnostic interface of the medical cable monitor;
activating the medical cable monitor in one mode of operation whereby signal processing circuitry of the medical cable monitor tests the functionality of the second medical cable connected between the second input interface and the second cable diagnostic interface.

10. The method according to claim 2 further comprising performing a zero/rezero function to short circuit the monitoring signal and create a zero voltage signal.

* * * * *